United States Patent
Ye et al.

(10) Patent No.: US 11,912,793 B2
(45) Date of Patent: Feb. 27, 2024

(54) POLYPEPTIDE AND APPLICATION THEREOF IN BONE REPAIR

(71) Applicant: SICHUAN UNIVERSITY, Chengdu (CN)

(72) Inventors: Ling Ye, Chengdu (CN); Fanyuan Yu, Chengdu (CN); Jiayi Wu, Chengdu (CN); Feifei Li, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/308,695

(22) Filed: Apr. 28, 2023

(65) Prior Publication Data

US 2023/0357321 A1    Nov. 9, 2023

(30) Foreign Application Priority Data

May 9, 2022 (CN) .......................... 202210496588.9

(51) Int. Cl.
 *C07K 7/08* (2006.01)
 *A61F 2/28* (2006.01)
(52) U.S. Cl.
 CPC .............. *C07K 7/08* (2013.01); *A61F 2/2846* (2013.01)
(58) Field of Classification Search
 None
 See application file for complete search history.

(56) References Cited

FOREIGN PATENT DOCUMENTS

CN     114656526    *    6/2022

OTHER PUBLICATIONS

CN 114656526 translation (retrieved from https://worldwide.espacenet.com/patent/search/family/082036503/publication/CN114656526A?q=CN114656526 on Oct. 24, 2023, 6 pages) (Year: 2023).*
CN 114656526 bibliographic information (retrieved from https://worldwide.espacenet.com/patent/search/family/082036503/publication/CN114656526A?q=CN114656526 on Oct. 24, 2023, 1 page) (Year: 2023).*
China White Paper on Osteoporosis, Chinese Journal of Health Management, 2009, pp. 148-154, vol. 3, No. 3.

* cited by examiner

*Primary Examiner* — Ronald T Niebauer
(74) *Attorney, Agent, or Firm* — Bayramoglu Law Offices LLC

(57) ABSTRACT

A polypeptide and an application thereof in bone repair are provided. An amino acid sequence of the polypeptide provided by the invention is shown as SEQ ID NO: 1. The invention further discloses use of the polypeptide GS18 in bone injury and/or bone repair. Furthermore, the invention further discloses an application of the polypeptide GS18 as well as a polypeptide scaffold for bone repair. The polypeptide of the invention demonstrates the ability to translocate β-catenin into the nucleus and induce the expression of secreted protein osteocalcin in vivo. In vitro, the polypeptide facilitates the osteogenic differentiation of osteogenesis-oriented BMSCs (pre-osteoblasts thereby promoting the process of bone repair.

5 Claims, 3 Drawing Sheets
Specification includes a Sequence Listing.

SEQUENCE LISTING

```
Sequence total quantity: 2
SEQ ID NO: 1            moltype = AA  length = 18
FEATURE                 Location/Qualifiers
REGION                  1..18
                        note = The sequence is synthetized
source                  1..18
                        mol_type = protein
                        organism = synthetic construct
SEQUENCE: 1
GPGGDKCRCV FHWCCYVS                                                  18

SEQ ID NO: 2            moltype = AA  length = 14
FEATURE                 Location/Qualifiers
REGION                  1..14
                        note = The sequence is synthetized
source                  1..14
                        mol_type = protein
                        organism = synthetic construct
SEQUENCE: 2
CKPLRLSKEE HPLK                                                      14
```

POLYPEPTIDE AND APPLICATION THEREOF IN BONE REPAIR

CROSS REFERENCE TO THE RELATED APPLICATIONS

This application is based upon and claims priority to Chinese Patent Application No. 202210496588.9, filed on May 9, 2022, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBTW001_Sequence_Listing.xml, created on Apr. 10, 2023, and is 3,366 bytes in size.

TECHNICAL FIELD

The invention belongs to the technical field of biological medicine and relates to an artificially synthesized polypeptide GS18 that may promote bone repair.

BACKGROUND

Bone defects are a common clinical disease. According to the data from the "China White Paper on Osteoporosis", there are about 3 million new patients with bone injury each year in China, which poses a huge burden on public health. Bone defects may be caused by a variety of etiologies, including trauma, infection, tumors, senescence, and so on. Although bone tissue has a strong ability to self-repair, reconstruct, and regenerate, large defects are often accompanied by outcomes such as bone nonunion, dysfunction, delayed healing, and even disunion. Therefore, advanced interventions are required to restore the structure and function of the damaged bone tissue.

Autologous bone transplantation is considered to be the gold standard for repairing bone defects. However, the application of autografts has certain limitations, such as donor site morbidity, a lack of donor sources, and an increased risk of infection. Allogeneic bone transplantation, using bone tissue from other patients, may present a promising avenue for addressing the deficiencies of autografts. Allografts confer osteoinductive properties and furnish growth factors crucial to stimulate bone regeneration. However, this method also faces a series of challenges such as resource constraints and ethical considerations. Currently, bone tissue engineering using inorganic non-metallic or polymeric scaffolds has received widespread attention. The incorporation of personalized scaffolds through 3D printing technology displays promising results in defect area matching. The porous structure of the scaffolds provides a guiding matrix for cell angiogenesis toward the desired bone regeneration outcomes. However, bone tissue engineering highly relies on the seed cells and cytokines that are encapsulated to recruit and induce the proliferation and differentiation of repair cells (such as bone marrow mesenchymal stem cells (BMSCs)). Among the medications that are currently approved by FDA to promote new bone formation, parathyroid hormone (PTH) may cause osteosarcoma when ingested in high doses. Bone morphogenetic protein (BMP2) has a short half-life and may lead to ectopic bone formation, osteolysis, and local inflammatory reactions. Therefore, it is still imperative to develop efficacious and non-hazardous agents for the enhancement of osteogenesis.

SUMMARY

The purpose of the invention is to overcome the shortcomings of the aforementioned prior art and provide an artificially synthesized polypeptide that may promote bone repair.

To achieve the above purpose, the technical solutions adopted by the invention are:
the invention provides a polypeptide, where an amino acid sequence of the polypeptide is shown in SEQ ID NO: 1.

The polypeptide of the invention contains 18 amino acids, with an amino acid sequence GPGGDKCRCVFHWVCCYVS, i.e. Gly Pro Gly Gly Asp Lys Cys Arg Cys Val Phe His Tip Cys Cys Tyr Val Ser. The inventors name the polypeptide GS18, and the following polypeptide uses this name.

The polypeptide GS18 of the invention has a molecular weight of 2017.33 Da.

The polypeptide GS18 of the invention may be synthesized using conventional synthesis methods, such as liquid-phase segmented synthesis, solid-phase synthesis, biosynthesis method, etc. As a preferred implementation, GS18 is synthesized using a solid-phase polypeptide synthesis process. Moreover, to ensure biological safety, the purity of GS18 must attain a minimum threshold of 95%. Products can be purified using HPLC.

The polypeptide GS18 of the invention may be used for bone repair and/or bone regeneration. It is suitable for treating various types of bone defects, such as segmental bone defects, trauma-induced bone injuries, tumor-induced bone defects, etc.

As a non-limiting embodiment of the present invention, GS18 can be utilized in conjunction with a tissue engineering scaffold to treat bone injury and/or facilitate bone repair. Additionally, GS18 can be incorporated into various bone repair scaffolds to be implanted into the bone defects. Such bone repair scaffolds may include but are not limited to, cement, electrospun scaffolds, hydrogels, etc.

GS18 can accelerate bone repair and promote bone regeneration via loading onto tissue engineering scaffolds. This effect can be extrapolated to encompass all extant tissue engineering scaffolds, including both biodegradable and non-biodegradable bone tissue engineering scaffolds.

The invention further discloses use of GS18 in activating β-catenin nuclear translocation and promoting osteocalcin expression.

In vitro osteogenic differentiation assay showed that GS18 could promote osteogenesis-oriented BMSCs (pre-osteoblasts) to form mineralized deposits, thereby promoting bone formation.

In SD rat cranial defects, GS18-modified GelMA was implanted into the defect sites and fitted seamlessly with the surrounding tissue. After 4 weeks, the cranial bones were harvested. H&E staining of histological sections suggested that GS18 could attract and recruit cells into the defects. According to Goldner's trichrome staining, the GS18-modified GelMA significantly promoted the formation of fibrous tissue within the defect area, as well as new bone formation with better calcification.

GS18 is designed based on the amino acid sequence of human-originated WNT3A ligand, which is recognized by its receptors Frizzled proteins and/or its co-receptors low-density lipoprotein receptor-related protein 5/6 (LRP5/6). Wnt3A can activate the canonical Wnt pathway, facilitate β-catenin to transfer into the nucleus and initiate transcription of downstream functional genes.

Furthermore, through tissue sections and immunofluorescence staining, it was found that active (non-phosphorylated) β-catenin (ABC) was abundantly expressed within the newly formed tissues in the calvarial defects, indicating successful translocation of β-catenin into the nucleus mediated by GS18. Meanwhile, the secreted protein osteocalcin (Ocn) was robust and widespread in the defect area. The presence of numerous $ABC^+$ $Ocn^+$ cells suggested that the promotion of osteogenesis by GS18 may occur through the activation of the Wnt/β-catenin pathway.

That is, GS18 is capable of activating β-catenin nuclear translocation and promoting the secretion of osteocalcin (Ocn), thereby effectuating the restoration of the structure and function of the bone injuries.

As a particularly advantageous embodiment of the GS18 application, the concentration range is set to be between 25 to 150 μg/mL, with a preferred range of 100 to 150 μg/mL.

Moreover, the invention discloses a bone repair composition containing a therapeutically effective dose of GS18 and a tissue engineering scaffold.

As a preferred solution, the invention further discloses a polypeptide scaffold modified by GS18. Preferably, the polypeptide scaffold can be bio-ceramics, metals, carbon-based compounds, biodegradable polymer composites, etc.

Moreover, the biodegradable polymer composite hydrogel scaffold is preferably to be sodium alginate, chitosan, hyaluronic acid, methacrylic anhydride gelatin (GelMA), etc.

As a preferred solution, GS18 is uniformly dispersed in the methacrylic anhydride gelatin (GelMA) scaffold in the current invention.

As a preferred solution, the concentration of GS18 in the scaffold is recommended to be between 25 to 150 μg/mL, with a preferred range of 100 to 150 μg/mL.

GelMA, a photosensitive biomaterial, exhibits excellent functionality when mixed uniformly with functional factors in liquids such as water, GelMA demonstrates outstanding operability and is capable of rapidly cross-linking to form three-dimensional structures upon exposure to photoinitiators. GelMA demonstrates superior biocompatibility and has inherent cell adhesion sites, which may promote cell proliferation and migration.

The GS18-modified GelMA can be readily fashioned into various geometries utilizing either a mold or 3D printing technology, to conform to the shape of the bone defect. The mechanical properties of the resultant structure can be easily tailored by adjusting the degree of substitution and concentration of GelMA, allowing for the provision of optimal elastic modulus, strength, and support, thereby facilitating the regeneration of the damaged bone tissue and partial restoration of its functionality.

Preferably, GS18 can be applied in the management of bone injury and/or the formulation of bone regenerative compositions.

The beneficial effects of the invention are:
1) the polypeptide GS18 of the invention can promote osteogenesis-oriented BMSCs (pre-osteoblasts) to form mineralized deposits, thereby promoting bone formation.
2) the polypeptide GS18 of the invention exhibits an attractive capability to recruit cells into bone repair materials (such as scaffolds, etc.). This feature accelerates the reparative and regenerative processes of bone defects, rendering GS18 a functional factor in the field of bone tissue engineering.
3) the polypeptide GS18 of the invention can translocate β-catenin into the nucleus, and promote the secretion of osteocalcin (Ocn), thereby promoting a repair process of bone injury due to the activation of canonical Wnt signaling pathway.
4) the polypeptide GS18 of the invention exhibits strong physiological activity, rapid and efficient localized tissue absorption, and low immunogenicity. These properties suggest that GS18 has the potential to serve as a superior substitute for osteogenic proteins.
5) the polypeptide GS18, as disclosed in the present invention, is classified as a small-molecule polypeptide, which can be synthesized using a straightforward process, resulting in a low production cost and high yield. GS18 demonstrates a high conversion value and versatile applications. Its promising clinical prospects make it a valuable therapeutic agent.

BRIEF DESCRIPTION OF THE DRAWINGS

FIG. 2A Mold; FIG. 2B. The materials taken out from the mold (diameter=5 mm, thickness=1 mm); FIG. 2C Bilateral calvarial defects before and after hydrogels implantation; FIG. 2D Cranial bones harvested 4 weeks after the surgery with hydrogels retained in the defects.

DETAILED DESCRIPTION OF THE EMBODIMENTS

The following is a further description of the specific embodiments of the invention in combination with embodiments and does not, therefore, limit the invention to the scope of the examples described.

Embodiment 1 In Vitro Cell Experiment 1.1 Cell culture: primary bone mesenchymal stem cells (BMSCs) extracted from the long bones of 3-week-old C57BL/6 male mice were selected, cultured at 37° C. in a humidified atmosphere with 5% $CO_2$, and inoculated into a 24-well plate with 30000 cells/well. α-MEM supplemented with 5% FBS, 1% penicillin-streptomycin, 10 dexamethasone, 10 mM β-glycerophosphate, and 50 μg/mL L-ascorbic acid was used as the osteogenic medium (OM) for osteogenic induction.

1.2 Cell induction: BMSCs were pretreated with OM for 5 days to achieve a determined osteogenic precursor cell state, followed by ongoing induction with peptide-containing OM for another 14 days. The experimental group used OM added with GS18, and the control group used OM added with the control peptide. GS18 was synthesized using a solid-phase polypeptide synthesis and was purified by HPLC (purity=96.59%). The amino acid sequence of the control peptide was shown as SEQ ID NO: 2, i.e. CKPLRLSKEEHPLK. The control peptide also adopted a solid-phase polypeptide synthesis method and used HPLC to purify products (purity=96.15%). The control peptides in the following embodiments all used this amino acid sequence.

1.3 Result verification: after osteogenic induction, the cells were fixed with 4% paraformaldehyde, stained with Von kossa in dark for 20 min, and colored by ultraviolet irradiation. A stereoscopic microscope (Olympus) was used for full-well photography, and an optical microscope (Olympus) was used for local magnification photography. The integrated density of calcium nodes (IntDen) and the percent of the calcified area to the total area (Area %) from five random areas were measured by Fiji. **$p<0.01$.

Figure 1:
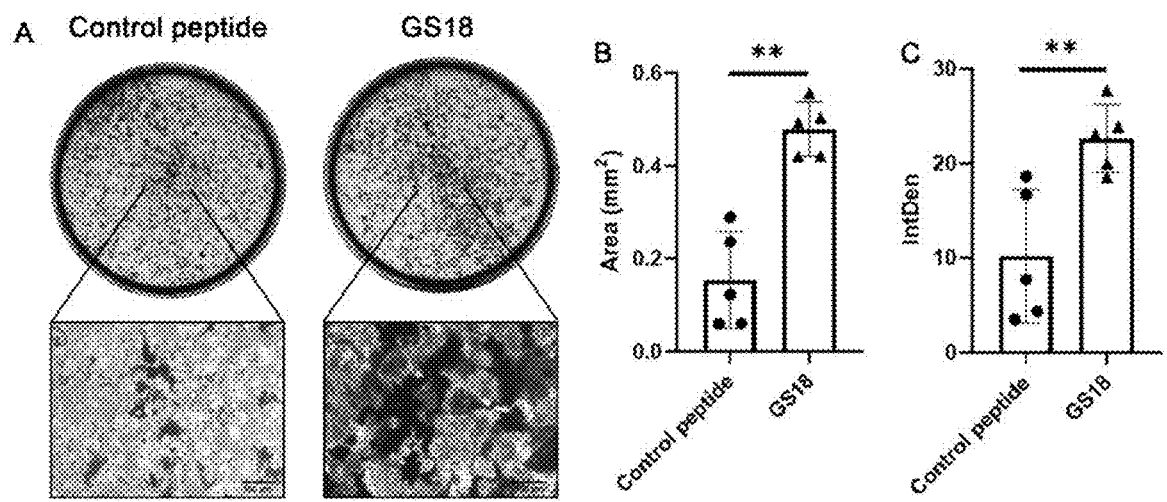
FIGS. 1A-1C are Von kossa stainings of osteogenesis-oriented BMSCs (pre-osteoblasts) after incubating in osteogenic medium with control peptide or GS18 for 14 days.

Von kossa staining results showed (FIGS. 1A-1C) that compared with the control peptide. GS18 significantly increased the formation (FIG. 1B) and maturation (FIG. 1C) of calcium deposits of pre-osteoblasts.

In sum, GS18 acted on osteogenesis-oriented BMSCs (pre-osteoblasts), and Von kossa staining confirmed its osteogenic inductive capacity in vitro.

In summary, this embodiment demonstrated that the polypeptide GS18 may promote osteogenesis-oriented BMSCs (pre-osteoblasts) to form mineralized deposits, thereby promoting bone formation.

Embodiment 2 Preparation of Polypeptide-Modified GelMA Hydrogel Scaffolds 2.1 GelMA Preparation: gelatin was fully dissolved in phosphate-buffered saline (PBS) at 60° C. with a concentration of 10% (w/v). 1.25% (v/v) methacrylic anhydride was added dropwise to the solution at 60° C. for 3 h. Double PBS was added to the mixture to stop the reaction. The solution was dialyzed against distilled water using 12-14 kDa dialysis tubing for 1 week. The obtained GelMA solution was frozen at −20° C. overnight and lyophilized for 72 h to get sponge GelMA.

2.2 Polypeptide modification: 2 g lyophilized GelMA was dissolved in 10 mL PBS containing 0.1% (w/v) photoinitiator LAP at 60° C. Then, either a control peptide or GS18 was added to achieve a final concentration of 0.1 mg/mL. The above mixture was injected into the mold (20 μL/hole) and exposed to ultraviolet irradiation (6.9 W/cm$^2$, 360-489 nm) for 2 min at room temperature. Once solidified, the materials were carefully detached from the mold and placed on ice for use.

2.3 Result verification: photographs were captured to depict the morphological characteristics of the polypeptide-modified GelMA after it was separated from the mold.

Figure 2:
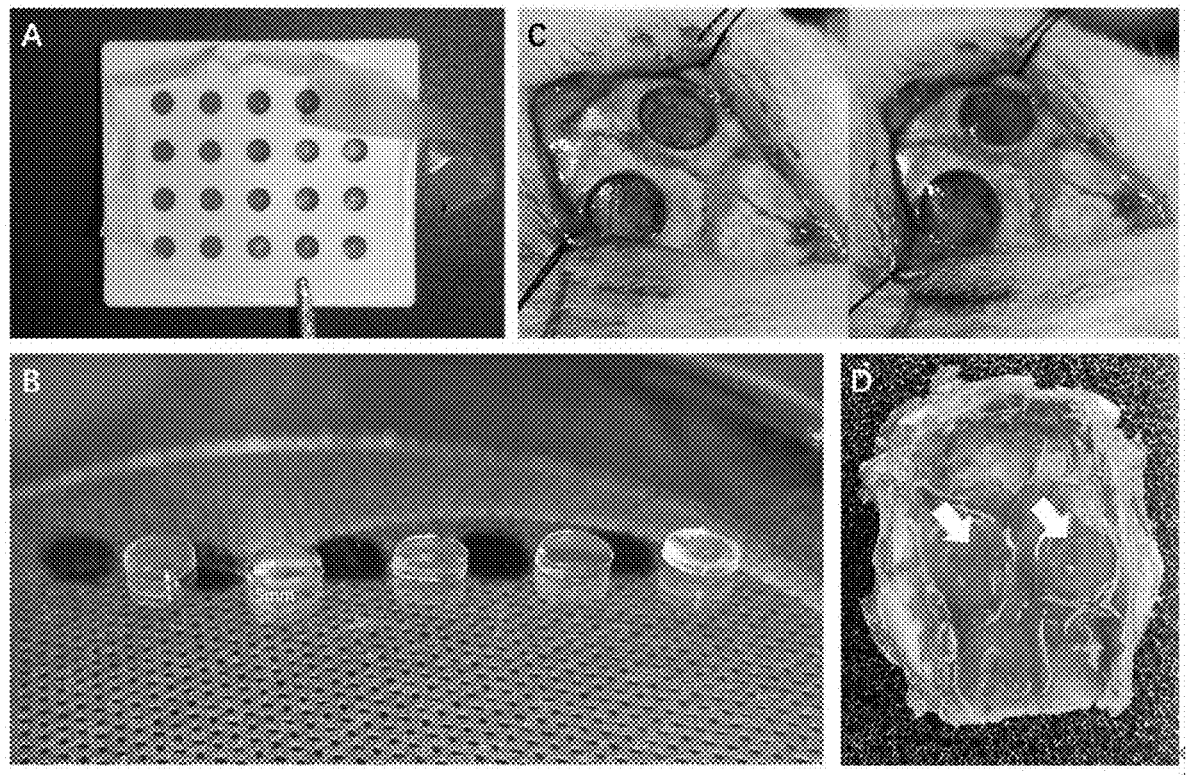
FIGS. 2A-2D are schematic illustrations of calvarial defect operation in SD rat.

The polypeptide-modified GelMA could be effectively demolded (FIG. 2A), and prepared into a cylindrical material with a 5 mm diameter and 1 mm thickness, featuring consistent dimensions in terms of size and thickness (FIG. 2B).

Embodiment 3 Bone Reparative Effects after Implantation of the Polypeptide-Modified GelMA into Calvarial Defects 3.1 Sample preparation: the GelMA scaffold was utilized to encapsulate either GS18 or control peptide at a concentration of 0.1 mg/mL, resulting in a total volume of 0.02 cm$^3$.

3.2 Animal model: 12-week-old SD male rats (about 320±20 g each) were used. Each group contained 3 rats. Rats were anesthetized with 2% pentobarbital via abdominal injection. The rats were positioned in the prone position. An electric razor was utilized to remove fur from the cranial region. Following this, the surgical sites were thoroughly cleansed with iodophor for disinfection. To maintain a sterile condition, disposable towels were carefully placed over the surgical regions. Starting from the nasal bone, a longitudinal skin incision of 1.5-2.0 cm was made along the midline of the top of the head. The subcutaneous tissue was gently separated with the handle of a surgical knife. The periosteum was meticulously incised along the sagittal suture of the cranium and subsequently separated to fully expose the parietal bone, occipital bone, and part of the frontal bone. Bilateral full-thickness circular calvarial defects (diameter=5 mm) were generated using a trephine. Sterilized materials were implanted into the defect sites. The experimental group was implanted with GS18-modified GelMA, While the control group was implanted with control peptide-modified GelMA. Finally, the skin was reset, sutured, and disinfected.

3.3 Tissue slices: after 4 weeks, the rats were sacrificed. The calvarial bones were harvested, fixed in 4% paraformaldehyde, decalcified with EDTA (12%, pH=7.0), dehydrated, embedded in paraffin, and cut into tissue slices with a thickness of 6 μm.

3.4 Result verification: photographs were captured to document the morphological characteristics of the GelMA scaffolds upon initial implantation, as well as their retention status after four weeks. The paraffin tissue slices were heated at 65° C., dewaxed, hydrated with xylene and gradient ethanol, and stained with H&E and Goldner's trichrome staining for histological evaluation.

FIGS. 2C-2D showed that GelMA scaffolds could fit seamlessly with the surrounding tissue (FIG. 2C) and remain in the defect sites 4 weeks after implantation (FIG. 2D). The periosteum was formed around the material to firmly wrap the scaffolds inside.

Figure 3:
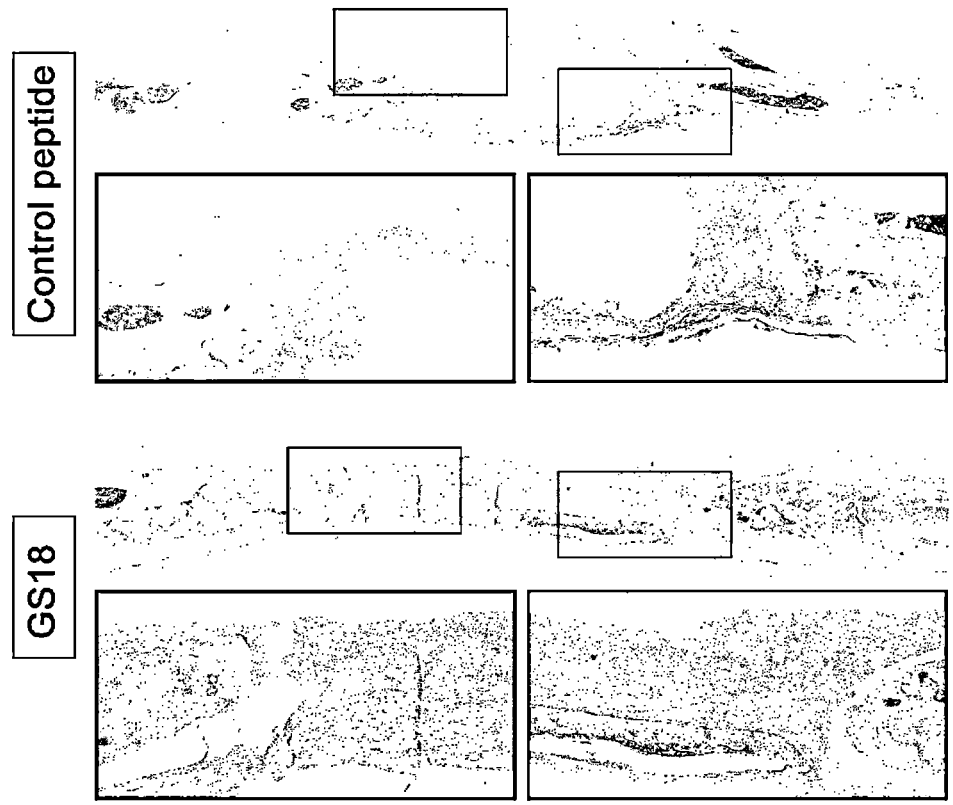
FIG. 3 is H&E staining of calvarial defects implanted with control peptide-modified GelMA or GS18-modified GelMA for 4 weeks.

The H&E staining (FIG. 3) showed that at 4 weeks post-implantation, the control peptide displayed the presence of fibrous tissue encircling the defect area, with a noticeable lack of cellular growth in the central region of the defect. GS18 demonstrated the capacity to attract and recruit cells into the scaffolds, leading to the establishment of fibrous tissue within the defect. Notably, the process was accompanied by a high degree of fiber mineralization and the emergence of constituents resembling those of bone tissue, indicating that polypeptide GS18 can ignite bone regeneration in vivo.

Figure 4:
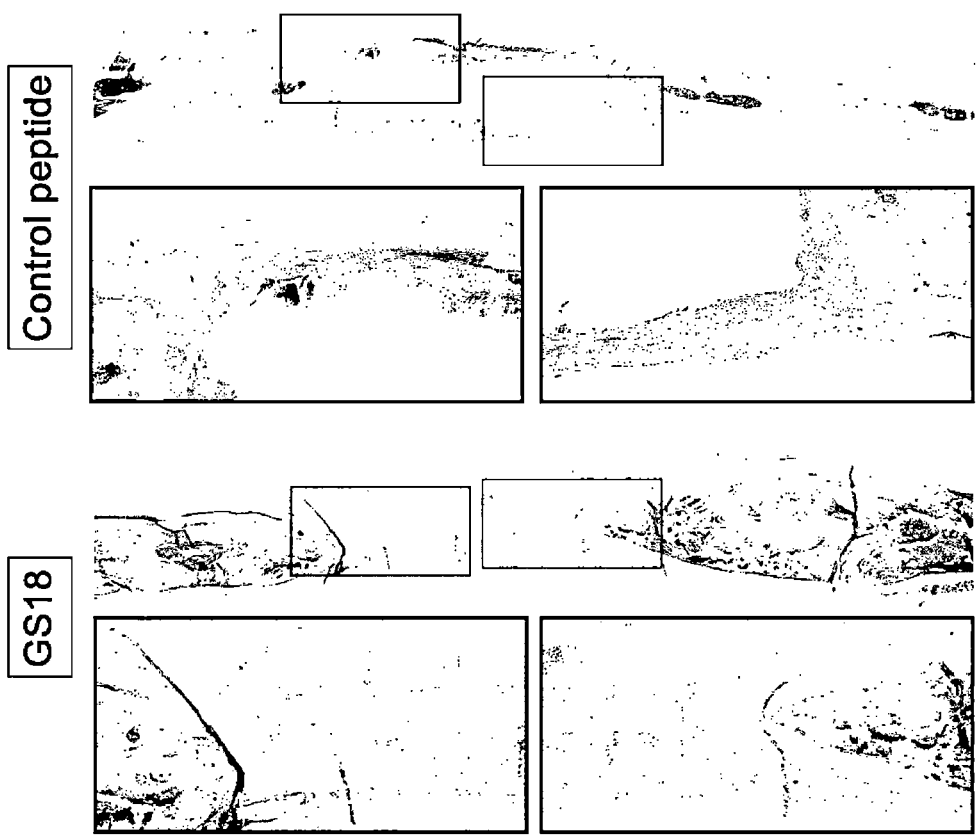
FIG. 4 is Goldner's trichrome staining of calvarial defects implanted with control peptide-modified GelMA or GS18-modified GelMA for 4 weeks.

Goldner's trichrome staining (FIG. 4) showed that the observation of the control peptide revealed the manifestation of fibrous tissue surrounding the defect site, accompanied by a conspicuous paucity of cellular growth within the central region of the defect. The GS18-modified GelMA exhibited remarkable cell-attracting and-recruiting properties, leading to the infiltration of a considerable number of cells into the defect area. The formation of green new bone further corroborated the substantial potential of GS18 in accelerating the reparative process of bone defects.

Embodiment 4 Activation of the Canonical Wnt Pathway Verified by Immunofluoreseence Staining 4.1 Antigen repair: the paraffin slices prepared in Embodiment 3.3 were heated at 65° C., dewaxed, hydrated with xylene and gradient ethanol, and immersed in the antigen repair buffer at 100° C. for 40 min. The slices were placed at room temperature. After cooling down to room temperature, the slices were soaked in PBS before staining.

4.2 Immunofluorescence staining: the slices were incubated in 0.5% PBST for 15 min, blocked for 20 min in PBST containing 5% BSA at room temperature, and incubated overnight at 4° C. with both rabbit monoclonal anti-Non-phospho (Active) β-Catenin (cell signaling #8814) and mouse monoclonal anti-osteocalcin (Santa Cruz sc-365797). The next day, the slices were washed with PBS for 30 min, and incubated with second antibodies as well as DAPI for 2 h at room temperature. Subsequently, the sections were washed with PBS three times for 15 min each time and sealed by the anti-fluorescence quencher.

4.3 Result verification: images of immunofluorescence staining were acquired using a confocal laser scanning microscope (CLSM, FV3000, Olympus, Japan).

Figure 5:
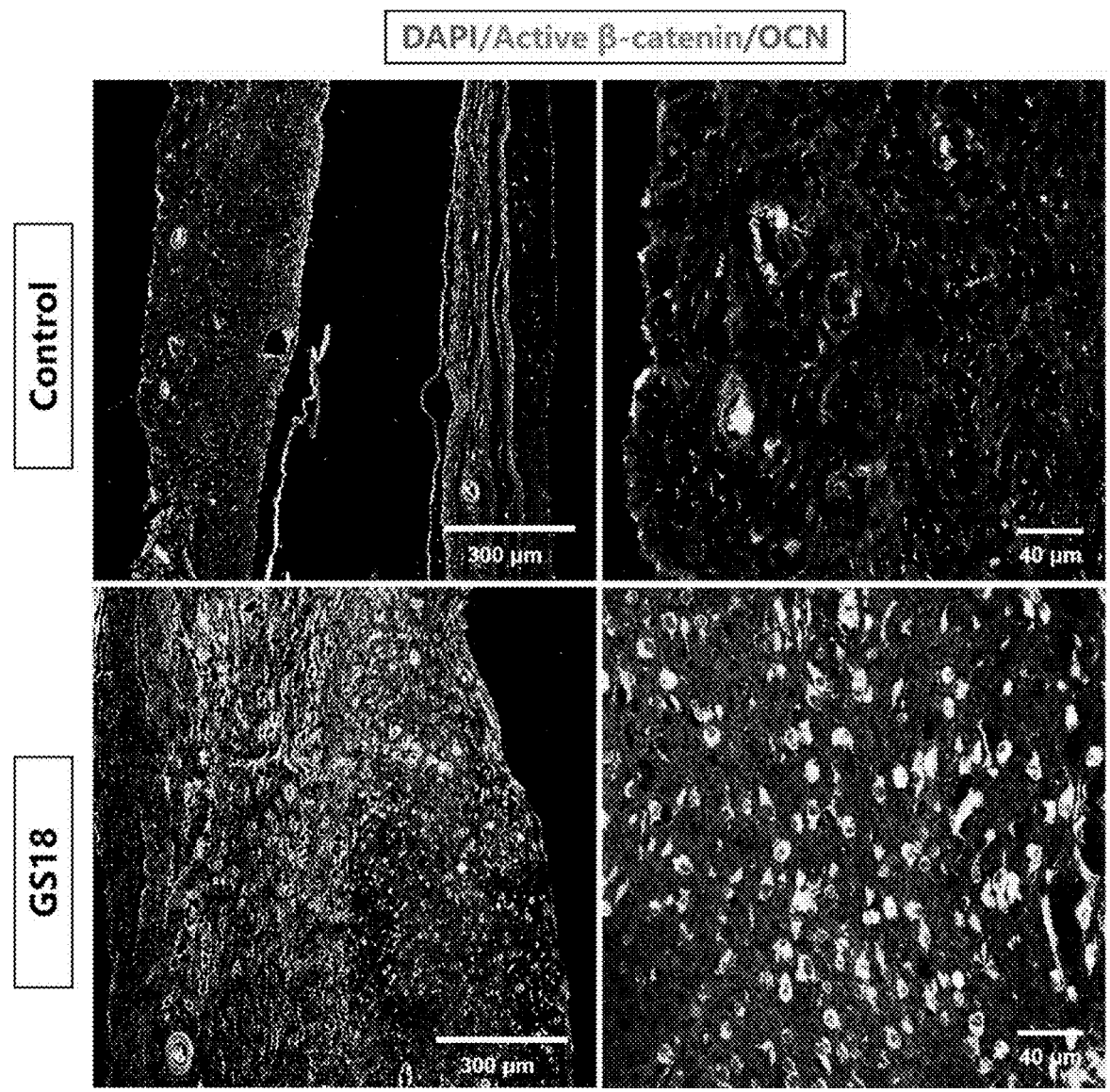
FIG. 5 is double-staining immumofluorescent images of active (non-phosphorylated) β-catenin (ABC) and osteocalcin (Ocn) in calvarial defects 4 weeks after implantation with non-peptide-modified GelMA (Control) or GS18-modified GelMA (GS18).

Immunofluorescence staining (FIG. 5) showed that the expression of active β-Catenin (in green) was significantly enhanced in the newly formed tissues of the calvarial defects treated with GS18, as compared to the control group where non-peptide-modified GelMA was implanted. This finding indicated the successful translocation of β-catenin into the nucleus mediated by GS18. Osteocalcin (Ocn), a non-collagenous bone matrix protein secreted during the final stages of osteoblast differentiation, is widely recognized as a prominent marker for bone formation. The robust and widespread expression of Ocn in the defect area of the GS18 suggested that the promotion of osteogenesis by GS18 might occur through the activation of the Wnt/β-catenin pathway.

What is claimed is:

1. A polypeptide, wherein an amino acid sequence of the polypeptide is shown in SEQ ID NO:1.

2. A bone repair composition, wherein the bone repair composition contains a therapeutically effective dose of the polypeptide of claim 1 and a tissue engineering scaffold.

3. A polypeptide scaffold, comprising the polypeptide of claim 1.

4. The polypeptide scaffold of claim 3, wherein the scaffold is a methacrylic anhydride gelatin scaffold; and a concentration of the polypeptide is 25 to 150 µg/mL.

5. A method bone repair, comprising the step of implanting a polypeptide scaffold comprising the polypeptide of claim 1 into a bone defect site. compositions.

\* \* \* \* \*